United States Patent [19]

Schneider

[11] Patent Number: 4,868,302

[45] Date of Patent: Sep. 19, 1989

[54] PROCESS FOR THE PREPARATION OF TAHP

[75] Inventor: Heinrich Schneider, Ingelheim am Rhein, Fed. Rep. of Germany

[73] Assignee: Boehringer Ingelheim KG, Ingelheim am Rhein, Fed. Rep. of Germany

[21] Appl. No.: 118,485

[22] Filed: Nov. 6, 1987

[30] Foreign Application Priority Data

Nov. 12, 1986 [DE] Fed. Rep. of Germany ....... 3638635

[51] Int. Cl.$^4$ ................... C07D 239/50; C07D 239/34
[52] U.S. Cl. .................................................... 544/320
[58] Field of Search ......................................... 544/320

[56] References Cited

U.S. PATENT DOCUMENTS 2,447,523  8/1948  Mozingo et al. .................... 544/320

Primary Examiner—John M. Ford
Attorney, Agent, or Firm—David E. Frankhouser; Daniel Reitenbach; Mary-Ellen M. Timbers

[57] ABSTRACT

The invention relates to an improved process for the catalytic hydrogenation of DAHNP and a new process for preparing 2,4-diamino-5-formylamino-6-hydroxypyrimidine.

6 Claims, No Drawings

PROCESS FOR THE PREPARATION OF TAHP

The invention relates to an improved process for the catalytic hydrogenation of 2,4-diamino-6-hydroxy-5-nitrosopyrimidine (DAHNP) and the reaction of the resulting 2,4,5-triamino-6-hydroxy-pyrimidine (TAHP) with formic acid to yield 2,4-diamino-5-formylamino-6-hydroxy-pyrimidine (DAFHP).

The catalytic hydrogenation of DAHNP is known and is described, for example, in U.S. Pat. No. 2,447,523. The process parameters are recited in this specification as follows. A 0.4 to 0.5 molar suspension of DAHNP in 0.1 to 1 N sodium hydroxide solution (corresponding to 0.2 to 2.5 mol NaOH per mol nitroso compound) is hydrogenated, using Pd, $PtO_2$ or Raney nickel as catalyst, under hydrogen pressures of from 1.4 to 2.3 bar.

When performing synthesis on an industrial scale, it is important not only to carry out a reaction with the highest possible yields but also to achieve the maximum possible throughput (measured in kg/h) or the maximum possible yield per unit of volume and time (kg/h l). This applies particularly to reactions in which the reactor volume cannot be altered without major expense, e.g. with reactions in autoclaves.

For a given reactor volume, the throughput of the process described in the U.S. patent is limited by the concentrations of DAHNP of 0.4 to 0.5 mol l specified in the patent specification. The concentrations of starting material cannot be increased substantially since the reaction mixture then thickens to such an extent that it is virtually impossible to stir and consequently the transition of the hydrogen into the liquid phase comes almost to a standstill. No improvement is brought about either by increasing the reaction temperature or by increasing the hydrogen pressure.

The aim of this invention is to provide a Process for the hydrogenation of DAHNP which permits a greater throughput with the same reactor volume.

According to the invention this is achieved by the fact that an aqueous, up to 3 molar suspension of DAHNP is hydrogenated in the presence of a suitable catalyst whilst a base is continuously metered in through the entire hydrogenation process. In general, the reaction is carried out under hydrogen pressures from 1.4 to 21 bar and at temperatures between 20° and 80° C.

The concentration of DAHNP is generally 0.5 to 3 mol/l, preferably 2 to 2.5 mol/l. Hydrogenation is preferably carried out at hydrogen pressures between 2 and 5 bar. Suitable hydrogenation catalysts are well known to those skilled in the art; $PtO_2$, Pd or Raney nickel are preferred, whilst Pd-charcoal with a Pd content between 1 and 10, preferably 2.5%, is particularly preferred, in a concentration of 0.02 to 0.2 g, preferably 0.1 g, palladium per mol of nitroso compound. The preferred temperature range is between 40° and 60° C.

The quantity of base added is not critical within wide limits; generally 0.8 to 1.5 mol of base are used per mol of DAHNP used, preferably 1.1 mol of base is used, suitably in the form of an aqueous solution. Preferred bases are alkali metal hydroxides such as NaOH or KOH. Another suitable base is ammonium hydroxide, for example. The base is added to the reaction mixture in the form of a 50% aqueous solution, for example, and is conveniently metered in continuously, in proportion to the conversion. The reaction may be carried out in any conventional pressurised reactor with stirring or mixing means but it is preferably carried out in a power jet-type loop reactor.

The free base of the 2,4,5-triamino-6-hydroxy-pyrimidine formed in the reduction is prone to oxidation and tends to discolor in air. As already known, TAHP can be isolated as a stable sulphate-hydrate in a virtually quantitative yield by the addition of sulphuric acid.

The advantage of the process according to the invention is the fact that the yield per unit of volume and time (kg/h l) is multiplied by almost six, with the same type of reactor, even though only about the same quantities of catalyst and base need be used.

A further advantage of the hydrogenation process according to the invention is obtained in the subsequent reaction of the resulting reaction product to form DAFHP. After the catalyst has been filtered directly off from the hydrogenation solution, the 2,4-diamino-5-formylamino-6-hydroxy-pyrimidine (DAFHP) is obtained in a practically quantitative yield by reaction with formic acid, optionally with the addition of an inorganic acid. Instead of the inorganic acid it is also possible to use a larger quantity of formic acid. This has two advantages. On the one hand, this makes it possible to use apparatus and equipment which is not made of materials resistant to inorganic acids and on the other hand the waste water is not contaminated with inorganic salts. In general, 1 to 3.5 mol, preferably up to 2.5 mol, more particularly 2 to 2.2 mol of formic acid and 0.8 to 1.5 mol of inorganic acid such as HCl or HBr are used per mol of DAFHP; instead of the inorganic acid it is also possible to use a total of 2 to 5 mol, preferably 3.3 to 4 mol, of formic acid per mol of DAFHP.

The reaction is carried out, for example, by taking the corresponding acid equivalents and adding the filtered hydrogenation solution, whereupon the reaction mixture heats up to about 80° to 90° C. The reaction to obtain the formyl compound is completed by further heating to 80° to 90° C. After cooling, the DAFHP is precipitated and isolated by known methods.

DAFHP can only be isolated in a reduced yield from not very highly concentrated solutions such as those obtained, for example, by the process of U.S. Pat. No. 2 447 523.

The following Examples are intended to illustrate the invention without restricting it.

EXAMPLE 1

In a stirred autoclave, 279 g of 2,4-diamino-6-hydroxy-5-nitrosopyrimidine, 10 g of 2.5% Pd-charcoal and 650 ml of water are placed, heated to 40° C. and 3 bar of hydrogen are introduced. For about 30 minutes, 158.4 g of 50% sodium hydroxide are continuously metered in at a maximum temperature of 50° C. The reaction mixture is then stirred into 312.4 g of well cooled 50% sulphuric acid through a pressure filter. After cooling to 10° C., the reaction mixture is suction filtered, washed with 2×450 ml of ice water and dried at 40° C. in a vacuum drying chamber under a weak hydrogen current.

Yield: 450.1 g of slightly violet-tinged crystals of 2,4,5-triamino-6-hydroxypyrimidine sulphate-hydrate corresponding to a yield of 97.3%

EXAMPLE 2

279 g of 2,4-diamino-6-hydroxy-5-nitroso-pyrimidine, 10 g of 2.5% Pd-charcoal and 650 ml of water are placed in a stirred autoclave heated to 40° C. and 3 bar of hydrogen are introduced. For about 30 minutes 134.6 g of 25% ammonia solution are metered in continuously at a maximum temperature of 50° C. The processing then continues as described in Example 1.

Yield: 448.3 g corresponding to 96.9% of theory.

EXAMPLE 3

279 g of 2,4-Diamino-6-hydroxy-5-nitroso-pyrimidine, 10 g of 2.5% Pd-charcoal and 650 ml of water are placed in a stirred autoclave and 1.4 bar of hydrogen are induced. For about 2 hours 158.4 g of 50% sodium hydroxide solution are metered in continuously at 20° to 25°. Treatment is continued as described in Example 1.

Yield: 449.2 g corresponding to 97.1% of theory.

EXAMPLE 4

279 g of 2,4-Diamino-6-hydroxy-5-nitroso-pyrimidine, 5 g of 1% Pd charcoal and 650 ml of water are placed in a stirred autoclave, heated to 70° C. and 21 bar of hydrogen are introduced. For about 30 minutes 158.4 g of 50% sodium hydroxide solution are metered in continuously at a maximum temperature of 80° C. Treatment is continued as described in Example 1.

Yield: 446.9 g corresponding to 96.6% of theory.

EXAMPLE 5

46.5 kg of 2,4-Diamino-6-hydroxy-5-nitrosopyrimidine, 1.5 kg of 2.5% Pd charcoal and 57.6 l of water are introduced into a VA-power jet loop reactor, heated to 40° C. and 5 bar of hydrogen are introduced. For about 30 minutes 26.5 kg of 50% sodium hydroxide solution are continuously metered in at up to 50° C. The reaction mixture is then added, through a lens filter, to a thoroughly cooled 250 liter enamel apparatus containing 104.1 kg of 50% sulphuric acid, with stirring. After cooling to 10° C. the mixture is centrifuged, washed with 2×75 l of water and dried at 40° C. in a vacuum drying cupboard.

Yield: 75.5 kg (97.9%) of 2,4,5-triamino--hydroxy-pyrimidine sulphate, hydrate.

EXAMPLE 6

After hydrogenation as described in Example 1, the reaction mixture is stirred to 182.2 g (220 mol) of formic acid through a pressure filter. After the addition of 254.6 g (110 mol) of 63% hydrobromic acid the mixture is heated to 85° C. for 2 hours. It is then cooled to 10° C., suction filtered and washed with 3×300 ml of water. After drying in a vacuum drying cupboard at 60° C., 296.0 g of 2,4-diamino-5-formylamino -6-hydroxypyrimidine are obtained (97.3% yield).

EXAMPLE 7

After hydrogenation as described in Example 1, the reaction mixture is stirred into 273.2 g (330 mol) of formic acid through a pressure filter. The resulting mixture is heated for 2 hours to 85° C., cooled to 10° C., suction filtered and washed with 2×300 ml of water. After drying in a vacuum drying cupboard at 60° C., 296.9 g of 2,4-diamino-5-formylamino-6-hydroxypyrimidine (97.6% yield) are obtained.

What is claimed is:

1. A process for the catalytic hydrogenation of 2,4-diamino-6-hydroxy-5-nitrosopyrimidine (DAHNP) in aqueous solution, characterized in that the concentration of DAHNP is about 0.5 to 3 mol l and a total of about 0.8 to 1.5 mol of base are added continuously, per mol of DAHNP, throughout the entire reaction time.

2. The process as claimed in claim 1, characterized in that an aqueous solution of KOH or NaOH is used as base.

3. The process as claimed in claim 1 characterized in that the hydrogenation is carried out at hydrogen pressures of between about 1.4 and 21 bar.

4. The process as claimed in claim 1, characterized in that the hydrogenation is carried out at temperatures of between about 20° and 80° C.

5. The process as claimed in claim 1, characterized in that Pd, Pd/C, PtO$_2$ or Raney nickel is used as the hydrogenation catalyst.

6. The process as claimed in claim 1, characterized in that the catalytic hydrogenation is carried out in a power jet-type loop reactor.

* * * * *